(12) United States Patent
Bachmann et al.

(10) Patent No.: US 7,901,419 B2
(45) Date of Patent: Mar. 8, 2011

(54) TELEMETRICALLY CONTROLLED BAND FOR REGULATING FUNCTIONING OF A BODY ORGAN OR DUCT, AND METHODS OF MAKING, IMPLANTATION AND USE

(75) Inventors: Michel Bachmann, Vaux sur Morges (CH); Alain Jordan, Ropraz (CH); Pierre Fridez, Crissier (CH); Jean-Charles Montavon, Lausanne (CH); Christian Imbert, Froideville (CH); Nikos Stergiopulos, Préverenges (CH)

(73) Assignee: Allergan, Inc., Irvine, CA (US)

( * ) Notice: Subject to any disclaimer, the term of this patent is extended or adjusted under 35 U.S.C. 154(b) by 1315 days.

(21) Appl. No.: 10/962,852

(22) Filed: Oct. 12, 2004

(65) Prior Publication Data

US 2005/0143765 A1    Jun. 30, 2005

Related U.S. Application Data

(63) Continuation-in-part of application No. 10/653,808, filed on Sep. 3, 2003, now Pat. No. 7,238,191.

(30) Foreign Application Priority Data

Sep. 4, 2002  (EP) .................................... 02019937

(51) Int. Cl.
*A61B 17/08* (2006.01)
*A61B 17/10* (2006.01)
(52) U.S. Cl. ............................ 606/157; 606/140; 600/37
(58) Field of Classification Search .................. 606/151, 606/140, 141, 157, 158; 600/37; 604/9
See application file for complete search history.

(56) References Cited

U.S. PATENT DOCUMENTS

| | | | |
|---|---|---|---|
| 2,163,048 A | | 6/1939 | McKee |
| 3,667,081 A | * | 6/1972 | Burger ........................ 15/250.24 |
| 3,840,018 A | | 10/1974 | Heifetz |
| 4,118,805 A | | 10/1978 | Reimels |
| 4,592,355 A | | 6/1986 | Antebi |
| 4,881,939 A | | 11/1989 | Newman |
| 5,074,868 A | | 12/1991 | Kuzmak |
| 5,226,429 A | | 7/1993 | Kuzmak |
| 5,449,368 A | | 9/1995 | Kuzmak |
| 5,601,604 A | | 2/1997 | Vincent |
| 5,658,298 A | | 8/1997 | Vincent et al. |
| RE36,176 E | | 3/1999 | Kuzmak |
| 5,938,669 A | | 8/1999 | Klaiber et al. |
| 6,074,341 A | * | 6/2000 | Anderson et al. ................ 600/29 |
| 6,102,678 A | | 8/2000 | Peclat |
| 6,102,922 A | * | 8/2000 | Jakobsson et al. ............. 606/157 |

(Continued)

FOREIGN PATENT DOCUMENTS

| | | |
|---|---|---|
| CN | 1250382 | 4/2000 |
| CN | 1367670 | 9/2002 |

(Continued)

*Primary Examiner* — Anhtuan T Nguyen
*Assistant Examiner* — Katherine M Dowe
(74) *Attorney, Agent, or Firm* — Stephen Donovan; Debra Condino

(57) ABSTRACT

Apparatus and methods are provided comprising an implantable non-hydraulic ring that encircles and provides a controllable degree of constriction to an organ or duct and an external control that powers and controls operation of the ring. The ring includes a rigid dorsal periphery that maintains a constant exterior diameter, and a compliant constriction system that reduces intolerance phenomena. A high precision, energy efficient mechanical actuator is employed that is telemetrically powered and controlled, and maintains the ring at a selected diameter when the device is unpowered, even for extended periods. The actuator provides a reversible degree of constriction of the organ or duct, which is readily ascertainable without the need for radiographic imaging. Methods of use and implantation also are provided.

42 Claims, 8 Drawing Sheets

U.S. PATENT DOCUMENTS

| | | | |
|---|---|---|---|
| 6,454,699 B1 * | 9/2002 | Forsell | 600/30 |
| 6,470,892 B1 | 10/2002 | Forsell | |
| 6,511,490 B2 | 1/2003 | Robert | |
| 6,547,801 B1 * | 4/2003 | Dargent et al. | 606/157 |
| 2002/0095181 A1 * | 7/2002 | Beyar | 606/232 |
| 2002/0139208 A1 * | 10/2002 | Yatskov | 74/424.77 |
| 2003/0073880 A1 | 4/2003 | Polsky et al. | |

FOREIGN PATENT DOCUMENTS

| | | |
|---|---|---|
| EP | 1396242 A1 | 3/2004 |
| EP | 1396243 A1 | 3/2004 |
| FR | 2797181 | 2/2001 |
| FR | 2797181 A1 | 2/2001 |
| FR | 2823663 | 10/2002 |
| FR | 2855744 | 12/2004 |
| WO | WO 00/15158 | 3/2000 |
| WO | WO 01/10359 A1 | 2/2001 |
| WO | WO 01/49245 A2 | 7/2001 |
| WO | WO03105732 | 12/2003 |
| WO | WO2004019671 | 3/2004 |

* cited by examiner

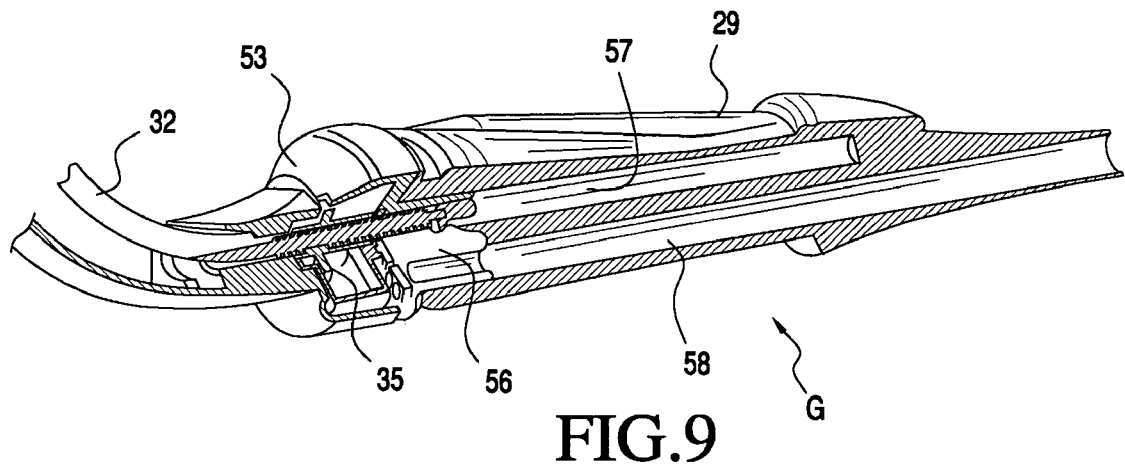
FIG.9
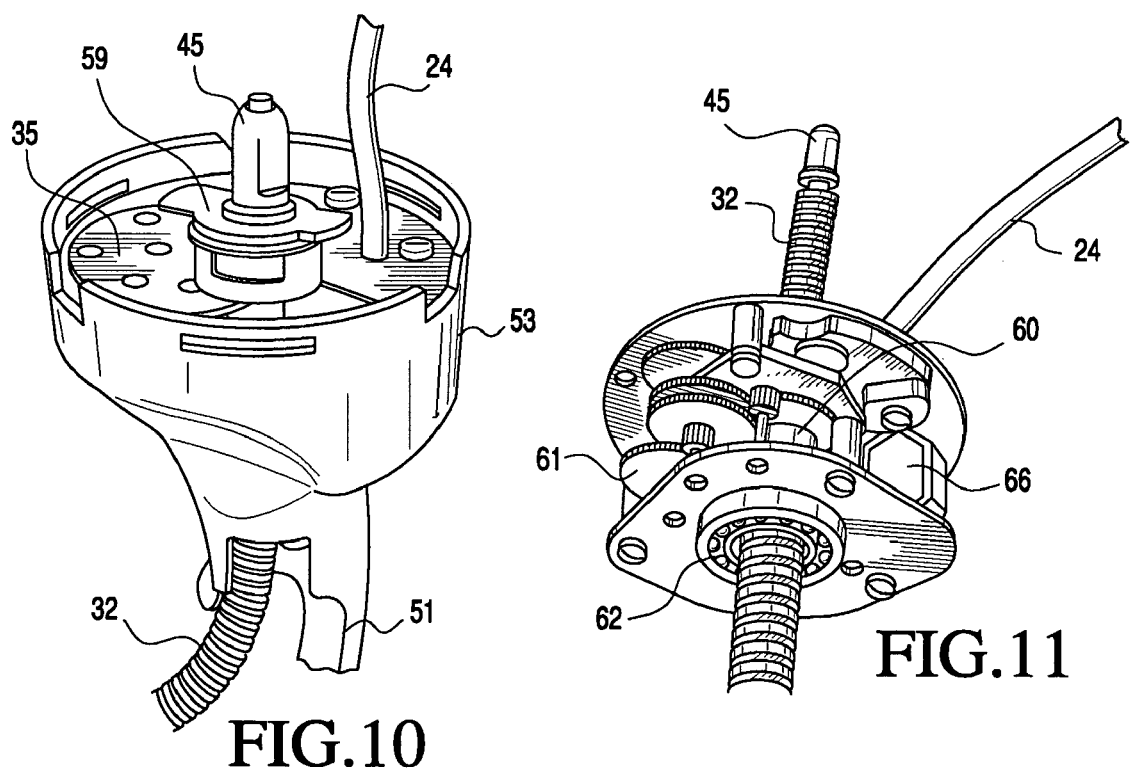
FIG.10
FIG.11

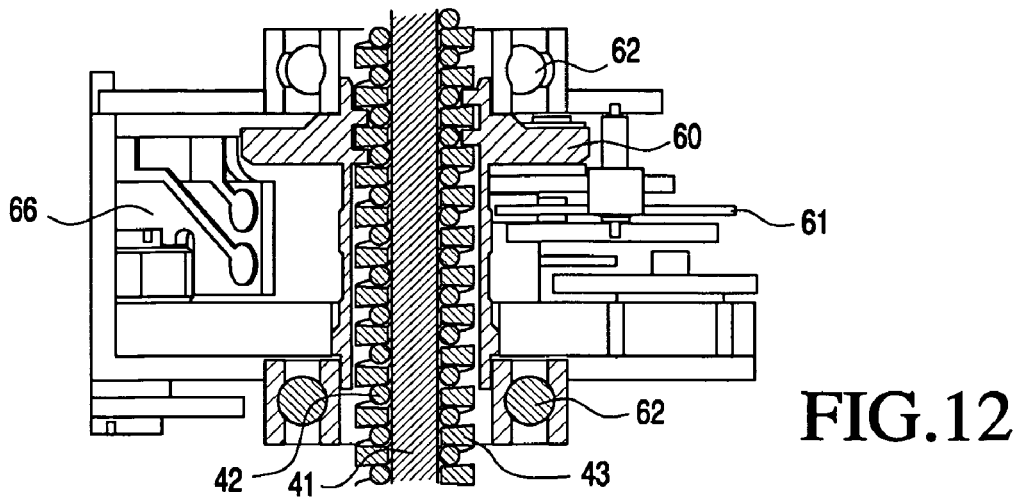
FIG.12
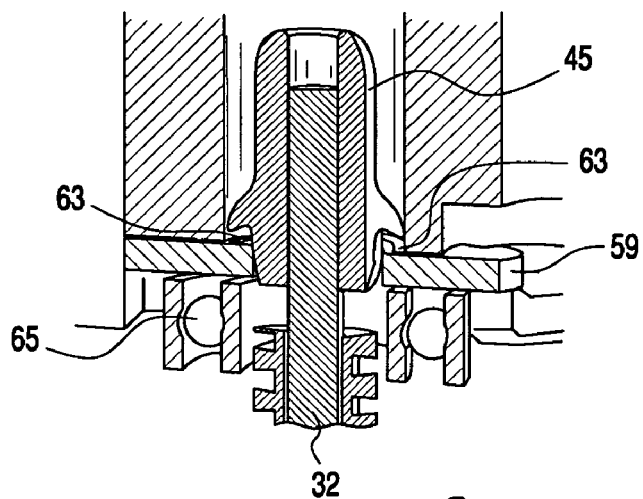
FIG.13
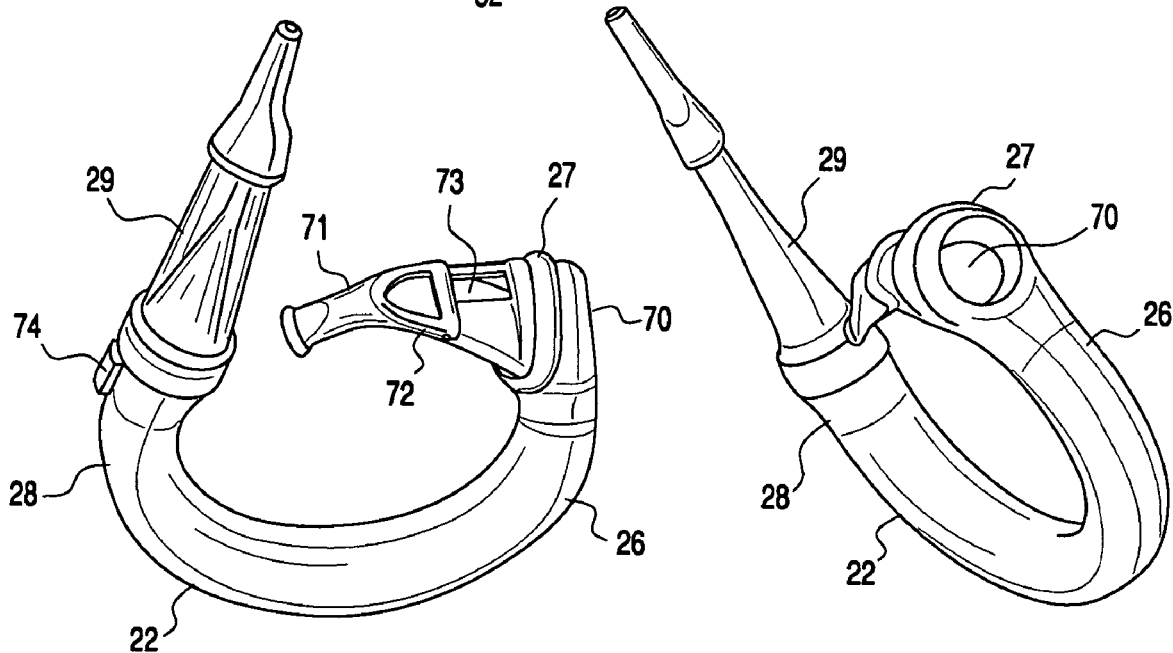
FIG.14A
FIG.14B

TELEMETRICALLY CONTROLLED BAND FOR REGULATING FUNCTIONING OF A BODY ORGAN OR DUCT, AND METHODS OF MAKING, IMPLANTATION AND USE

FIELD OF THE INVENTION

This invention relates to laparoscopic implants designed to be implanted in the body of a patient around a biological organ having a pouch or duct to regulate functioning of the organ or duct. More specifically, the present invention is directed to an implantable telemetrically-powered and controlled ring suitable for use as a gastric band to treat obesity or as an artificial sphincter.

BACKGROUND OF THE INVENTION

Obesity refers to a body weight that exceeds the body's skeletal and physical standards. One well recognized parameter used to measure obesity is not directly the weight but the Body Mass Index (BMI) because it takes into account patient height: BMI is calculated by dividing weight by height squared and is expressed in kg/m2.

Obesity is usually defined as a BMI of 30 kg/m2 or greater, and is further broken down into Class I (BMI of 30-34.9 kg/m2), Class II (BMI of 35-39.9 kg/m2) also called severe obesity, and Class III (BMI of 40 kg/m2 or greater), also called extreme obesity. Obesity is considered "morbid" when the BMI is over 40 (extreme obesity) or the BMI is over 35 (severe obesity) and serious comorbidities are present.

Obesity is well recognized as a serious health problem, and is associated with numerous health complications, ranging from non-fatal conditions to life threatening chronic diseases. According to the World Health Organization, the non-fatal, but debilitating health problems associated with obesity include respiratory difficulties, chronic musculoskeletal problems, skin problems and infertility. Life-threatening problems fall into four main areas: cardiovascular disease problems; conditions associated with insulin resistance such as type 2 diabetes; certain types of cancers, especially the hormonally related and large bowel cancers; and gallbladder disease. Beyond these physiological problems, obesity has also psychological consequences, ranging from lowered self-esteem to clinical depression.

Surgical intervention generally is the treatment of choice for patients afflicted with morbid obesity. Such intervention not only mitigates the myriad health problems arising from overweight, but may reduce the risk of early death of the patient. Left untreated, morbid obesity may reduce a patient's life expectancy by ten to fifteen years.

Morbidly obese patients as a group are poorly adapted to attain sustainable long-term weight loss using non-surgical approaches, such as strict diets combined with exercise and behavioral modification, even though such methods are acknowledged to be the safest. For this reason, there is a continuing need for direct intervention to provide effective, long-term treatments for morbid obesity.

Three main surgical procedures are currently in use: Roux-en-Y Gastric Bypass ("RYGB"), Vertical Banded Gastroplasty ("VBG") and Adjustable Gastric Banding ("AGB").

In RYGB a small stomach pouch is created and a Y-shaped section of the small intestine is attached to the pouch so that food bypasses the lower stomach, the duodenum and the first portion of the jejunum. The RYGB procedure is both restrictive, in that the small pouch limits food intake and malabsorptive, in that the bypass reduces the amount of calories and nutrients the body absorbs.

VBG employs a non-adjustable synthetic band and staples to create a small stomach pouch. AGB employs a constricting synthetic ring that is placed around the upper end of the stomach to create an artificial stoma within the stomach. The band is filled with saline solution and is connected to small reservoir/access-port located under the skin of the abdomen. The AGB band may be inflated, thereby reducing the size of the stoma, or deflated, thus enlarging the stoma, by puncturing the access-port with a needle and adding or removing saline solution. Both VBG and AGB are purely restrictive procedures, and have no malabsorptive effect.

An example of the AGB technique is described, for example, in U.S. Pat. No. 5,074,868 to Kuzmak. As described in that patent, a flexible band of elastomeric material is implanted around the stomach to form a closed loop defining a fixed pre-established diameter. The body of the flexible band includes an expandable chamber, which is linked via a tube to a subcutaneous injection port. Fluid may be introduced into the injection port using a syringe to add or remove fluid from the expandable chamber and thus vary the internal diameter of the band and the diameter of the stoma. In this way, expansion of the chamber, in combination with the pre-established and fixed diameter of the band, permits adjustment of the stoma diameter and thus regulation of the quantity of food ingested.

While the device described in the Kuzmak patent is capable of providing satisfactory results, it nevertheless-suffers from a number of drawbacks. The injection port is the source of many of the problems encountered with the hydraulic gastric bands, including infection, damage to the tube due to imprecise puncturing with the needle, discomfort to the patient created by the port and difficulty in locating the port (often necessitating the use of x-ray to determine the location and orientation of the port).

In addition, although the injection port makes it possible to make limited adjustments to the diameter of the ring without major surgical intervention, installation of the band may be accompanied by intolerance phenomena, such as vomiting. This drawback may arise from various causes, including too great a reduction in the diameter of the stoma, ineffective action of the band due to too great a stoma diameter, obstruction, infection or local or general inflammation.

Accordingly, it sometimes is necessary to re-operate, either to relieve the patient or to adjust or change the previously-implanted band. In such cases, the previously-implanted band must be cut and either removed or replaced, during operations that are difficult to carry out, difficult for the patient to tolerate and costly.

U.S. Pat. No. 5,938,669 to Klaiber et al. addresses some of the issues arising from use of an injection port, and describes a gastric band that is adjusted using a remote control in a non-invasive manner. The device includes a control box that is implanted in the body of the patient and coupled to the gastric band. The control box includes a battery-operated electric pump and valve that are coupled between an expandable chamber and a fluid reservoir. The control box also contains a radiofrequency transceiver and microprocessor, which are arranged to communicate with an external remote control to control operation of the pump to add or remove fluid from the reservoir to the expandable chamber, thereby selectively varying the diameter of the stoma opening. The external remote control is operated by a physician.

The device described in Klaiber presents an interesting and beneficial development for patients, but still suffers from a number of drawbacks. Implantation of that system's fluid reservoir into the body of the patient requires a delicate procedure, so as to avoid puncture and maintain watertightness.

Likewise, the introduction of a battery within the patient's body confers an undesirable degree of fragility upon the system. For example, further surgical intervention is required to replace a depleted or leaking battery.

Several attempts to overcome drawbacks associated with hydraulically-actuated gastric bands, such as described in the Kuzmak and Klaiber patents, are known in the art. For example U.S. Pat. No. 6,547,801 to Dargent et al. describes a surgically implanted gastroplasty system having a flexible tractile element that engages a motor-driven notched pulling member. The motor is powered and controlled by an inductive circuit, so that the diameter of the ring may only be changed by operation of the external remote control.

Although the system described in the Dargent patent overcomes problems associated with injection ports used in previously-known hydraulically-actuated bands and with systems requiring implantable batteries, it too is expected to suffer from a number of drawbacks. For example, while Dargent states that the gearing of the pulling member is sufficient to prevent the band from unwinding in the unpowered state, the pulling member configuration still may permit the tractile element to "jump" or slip if the band is subjected to compression. Further, as shown in the drawings of that patent, when the band contracts, ripples form in the interior surface of the band that may cause inflammation or abrasion of the stomach.

In addition, it has been observed that within a few weeks of implantation of a gastroplasty band, fibrous tissue tends to overgrow and encapsulate the band. It is expected that, as in Dargent, where the exterior of the diameter of the band contracts upon actuation of the motor, such fibrous tissue may interfere with proper functioning of the device. Finally, while the band described in Dargent is flexible, it has no ability to stretch, for example, as may be needed to accommodate convulsive motions of the stomach, e.g., during vomiting, and consequently may lead to patient intolerance problems.

All of the foregoing surgical techniques involve major surgery and may give rise to severe complications. Recent developments have focused on the use of laparoscopic implantation of the gastric ring to minimize patient discomfort and recuperation time.

For example, U.S. Pat. No. 5,226,429 to Kuzmak describes a hydraulically-controlled gastric band that is configured to be implanted using laparoscopic techniques. The band is specially configured to be inserted through a laparoscopic cannula, and includes an injection port to control the degree of constriction imposed by the band. As previously noted, however, that band is expected to suffer from the same drawbacks as previously-known hydraulic gastric bands. In addition, that patent provides no teaching or suggestion as to how non-hydraulically controlled gastic bands could be configured for laparoscopic implantation. For example, the patent provides no teaching that would enable a clinician to adapt the non-hydraulic device described in Dargent for laparoscopic implantation.

In view of the foregoing, it would be desirable to provide apparatus and methods for regulating functioning of a body organ or duct that provides high precision in a degree of constriction imposed upon the organ or duct, without the drawbacks associated with the use of previously-known injection ports.

It further would be desirable to provide apparatus and methods for regulating functioning of a body organ or duct that maintains a desired level of constriction over an extended period using a gear-driven arrangement that may be implanted laparoscopically.

It also would be desirable to provide apparatus and methods for regulating functioning of a body organ or duct that is capable of accommodating occasional convulsive motions of the organ or duct.

It further would be desirable to provide apparatus and methods for regulating functioning of a body organ or duct that is telemetrically powered, so as to avoid the need for re-operation to replace or repair a defective or depleted energy source.

It still further would be desirable to provide apparatus and methods for regulating functioning of a body organ or duct that is telemetrically controlled, provides a high degree of safety, and reliably imposes a reproducible degree of constriction.

It also would be desirable to provide apparatus and methods for regulating functioning of a body organ or duct that maintains a constant exterior diameter, and is not rendered inoperative by tissue ingrowth or fibrous tissue encapsulation.

It further would be desirable to provide apparatus and methods for regulating functioning of a body organ or duct that may be non-invasively, safely and easily adjusted by a physician, without the need for radiographic imaging.

SUMMARY OF THE INVENTION

In view of the foregoing, it is an object of the present invention to provide apparatus and methods for regulating functioning of a body organ or duct that provides high precision in a degree of constriction imposed upon the organ or duct, without the drawbacks associated with the use of previously-known injection ports.

It is a further object of the present invention to provide apparatus and methods for regulating functioning of a body organ or duct that maintains a desired level of constriction over an extended period using a gear-driven arrangement that may be implanted laparoscopically.

It is another object of this invention to provide apparatus and methods for regulating functioning of a body organ or duct that is capable of accommodating occasional convulsive motions of the organ or duct.

It is a further object of the present invention to provide apparatus and methods for regulating functioning of a body organ or duct that is telemetrically powered, so as to avoid the need for re-operation to replace or repair a defective or depleted energy source.

It is still another object of this invention to provide apparatus and methods for regulating functioning of a body organ or duct that is telemetrically controlled, provides a high degree of safety, and reliably imposes a reproducible degree of constriction.

It is yet another object of the present invention to provide apparatus and methods for regulating functioning of a body organ or duct that maintains a constant exterior diameter, and is not rendered inoperative by tissue ingrowth or fibrous tissue encapsulation.

It also is an object of this invention to provide apparatus and methods for regulating functioning of a body organ or duct that may-be non-invasively, safely and easily adjusted by a physician, without the need for radiographic imaging.

These and other objects of the present invention are accomplished by providing apparatus and methods wherein a non-hydraulic ring and associated implantable controller are laparoscopically implanted in the body of a patient, so that the ring encircles and provides a controllable degree of constriction to an organ or duct. The ring according to the present invention comprises a rigid dorsal peripheral portion that maintains a constant exterior diameter, and a spring portion that facilitates laparoscopic implantation of the device and provides a degree of compliance to permit convulsive motion of the organ or duct, thereby reducing intolerance phenomena.

In accordance with the principles of the present invention, the ring includes a high precision, energy efficient mechanical actuator that maintains the ring at a selected diameter, when the device is unpowered, for extended durations. The implantable controller is telemetrically powered and controlled, thereby eliminating the need for re-operation to repair or replace a defective or depleted energy source.

In a preferred embodiment, the ring includes a high precision motor that imposes a reversible degree of constriction of the organ or duct by actuation of the motor, wherein the degree of constriction is readily ascertainable without the need for radiographic imaging. The ring further comprises a flexible element having a predefined screw thread pitch that provides a high degree of precision, while retaining good flexibility. A contact is provided at the free end of the flexible element that mates with an electrical switch to establish a reference position for the ring in the fully opened position.

In addition, the ring comprises a soft and flexible ePTFE component, encapsulated in a leak-proof flexible membrane, that maintains a smooth contact surface with the organ or duct, thereby permitting the ring to undergo considerable diametral contraction without inducing ripples or bunching in the underlying organ or duct.

The ring of the present invention includes a non-invasive, simple to use external control that may be operated by the physician, and which may be adjusted during an in-office procedure without the need for radiographic confirmation. In addition, the ring and implantable controller are configured to be easily introduced through a commercially available 18 mm trocar and implanted using conventional laparoscopic techniques.

Methods of implanting the apparatus of the present invention also are provided.

BRIEF DESCRIPTION OF THE DRAWINGS

The foregoing and other objects of the invention will be apparent upon consideration of the following detailed description, taken in conjunction with the accompanying drawings, in which like reference characters refer to like parts throughout, and in which:

FIG. 9 is a cross-sectional view of an elastomeric housing of the gastric band depicting the path of the antennae wire and cavity that accepts the tension element;

FIG. 10 is a perspective view of the actuator housing, tension element and actuator of the present invention;

FIG. 11 is a perspective of the tension element engaged with the actuator;

FIG. 12 is a cross-sectional view depicting the construction of the actuator of FIG. 11;

FIG. 13 is a cross-sectional view depicting the construction of the reference position switch;

FIGS. 14A and 14B are perspective views illustrating the clip used to close the gastric band into a loop;

DETAILED DESCRIPTION OF THE INVENTION

Figure 1:
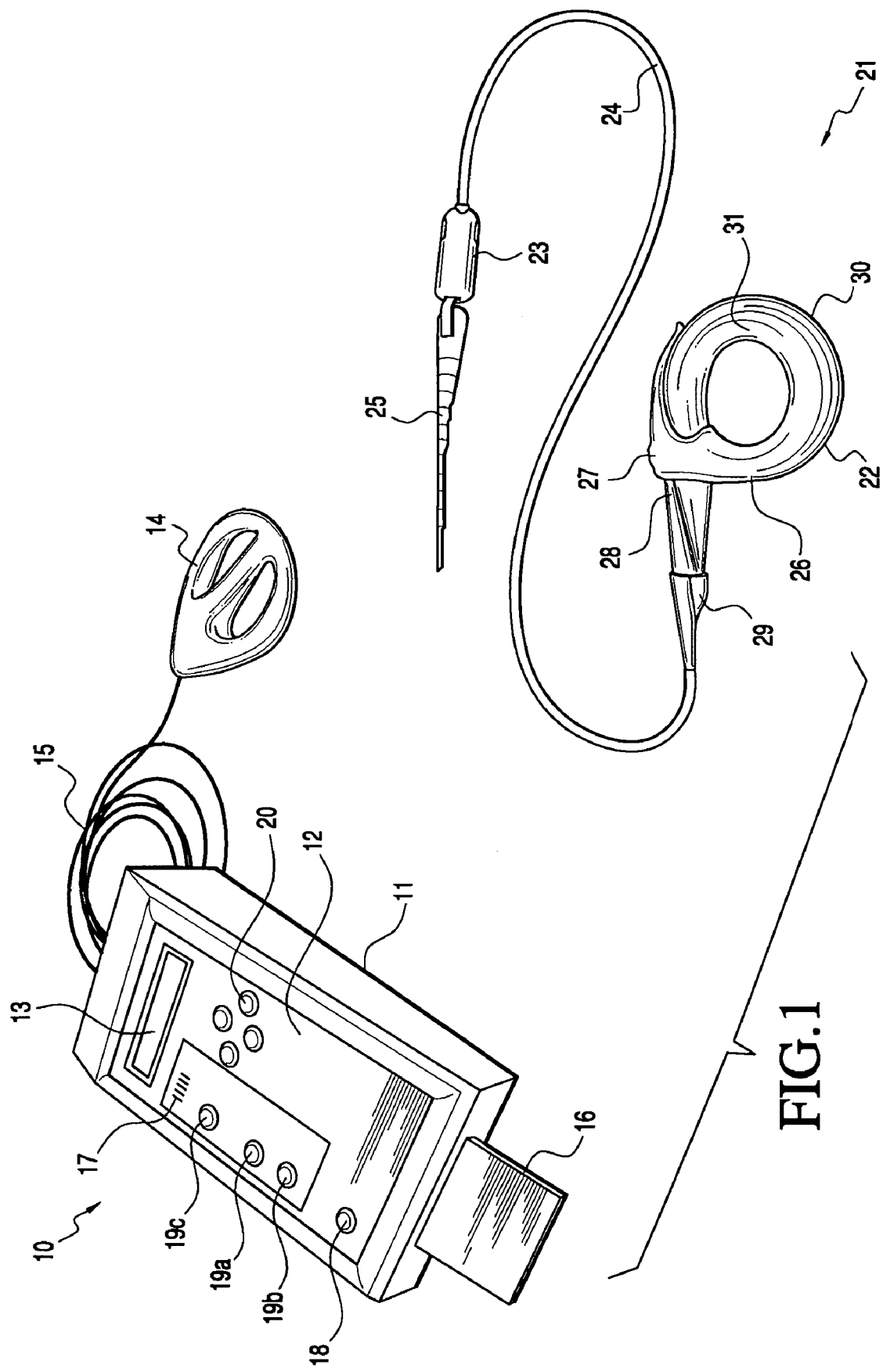
FIG. 1 is a perspective view of an exemplary ring system of the present invention including an external control and implantable ring.

Referring now to FIG. 1, the banding system of the present invention is described, comprising external control 10 and implantable gastric band 21. In the following description reference will be made, by way of illustration, to a gastric band designed to be implanted around the stomach to selectively adjust the diameter of opening of the stoma, and thereby control food intake. Such regulation has the effect of creating a feeling of satiety in the patient after relatively little food is consumed, and provides an effective treatment for morbid obesity.

It is to be understood, however, that the present invention is in no way limited to gastroplasty, but on the contrary, advantageously may be applied to regulate the functioning of other body organs or ducts, such as in the treatment of gastro-esophageal reflux disease, urinary or fecal incontinence, colostomy, ileostomy or to regulate blood flow in connection with isolated organ perfusion for treatment of cancer. For treatment of urinary continence, the implantable portion of the system will be implanted around the bladder or urinary tract, while in the case of fecal incontinence, the ring may be implanted around a portion of the gastro-intestinal tracts, such as anal structures of the intestine.

System Overview

With respect to FIG. 1, self-contained external control 10 comprises housing 11 having control panel 12 and display screen 13. External control 10 includes a digital signal processor and may be battery-powered or powered using an external power supply, e.g., connected to a wall socket. External antenna 14 is coupled to remote control 10 via cable 15. As described more fully with respect to FIG. 18, external control 10 includes a microprocessor that controls the emission of radiofrequency signals to the gastric band 10 to both control and power operation of the band.

External control 10 accepts patient microchip card 16, which corresponds to the specific gastric band implanted in the patient, and stores data, such as the implant identification number, adjustment parameters (e.g., upper and lower limits of an adjustment range, etc.) and information regarding the last adjustment position of the ring. External control 10 includes signal strength indicator 17, as described hereinbelow with respect to FIG. 19, ON/OFF button 18, OPEN button 19a, CLOSE button 19b, COUPLING button 19c and menu options panel 20.

During use of the device, the physician need only turn external control 10 ON using button 18, position external antenna 14 over patient's chest above antenna/controller pod 23, check the coupling by depressing COUPLING button 19c, and when the coupling is sufficient, adjust the degree of constriction using OPEN button 19a or CLOSE button 19b. The diameter of the band is continually displayed on display panel 13 with a precision of about 0.1 mm for the entire range of diameters of the ring, e.g., from 19 mm fully closed to 29 mm fully opened.

Still referring to FIG. 1, gastric band 21 of the present invention now is described, and includes ring 22 coupled to implantable antenna/controller pod 23 via cable 24. Pod 23 includes removable tag 25 that may be used to laparoscopically position ring 22. Ring 21 includes first end 26 having clip 27 that slides over and positively engages second end 28 of the ring.

As described in detail below, ring 22 is configured to be straightened to pass through the lumen of a commercially available 18 mm trocar for delivery in a patient's abdomen. Tag 25, pod 23 and cable 24 then are passed through clip 27 to form the ring into a substantially circular loop around an upper portion of the patient's stomach, thereby reducing the diameter of the opening of the stomach. In its undeformed shape, ring 22 assumes a circular arc configuration that facilitates positioning of the ring around the stomach and also in self-guiding the clipping procedure.

Ring 22 of the present invention comprises a flexible tubular band having a smooth, flexible and elastic membrane, thus ensuring atraumatic contact with the patient's stomach tissue that is easily tolerated. When engaged with dorsal element 38, membrane 39 is stretched by an appropriate factor (i.e., 20%-40%), so that when ring 22 is in its fully closed position, little or no wrinkling appears on the membrane surface. Ring 22 has approximately the shape of a torus of revolution of substantially cylindrical cross-section. Alternatively, ring 22 may have any other suitable cross-section, including rectangular. Housing 29 on second end 28, clip 27 on first end 26 and dorsal peripheral portion 30 of ring 22 (indicated by the darker portions of ring 22 of FIG. 1), preferably comprise a biocompatible material such as silicone. Interior portion 31 of ring 22 preferably comprises expanded polytetrafluoroethylene (ePTFE), which permits longitudinal contraction without bunching or ripples, and is covered by a thin membrane of protective material, for example, based on or made of silicone.

Advantageously, as depicted in FIG. 1, portions of ring 22 employ polymeric components having different colors to facilitate laparoscopic manipulation and implantation. In one preferred embodiment, interior portion 31 of the ring comprises lighter colored materials while the clip 27 and housing 29 comprise darker colored materials, thereby indicating to the clinician which portions of ring 22 may be grasped during implantation. In particular, the colors may consist of black, white and different shades of gray achievable with implantable silicone.

Implantable Ring

Figure 2A:
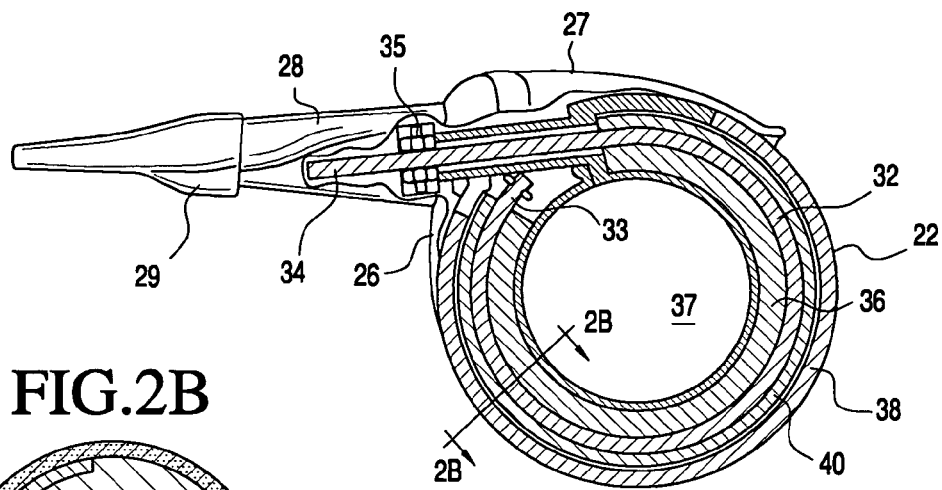
FIGS. 2A and 2B are, respectively, a schematic diagram, partly in cross-section, of the gastric band of FIG. 1 and a sectional view taken along line 2B-2B of FIG. 2A.
Figure 2B:
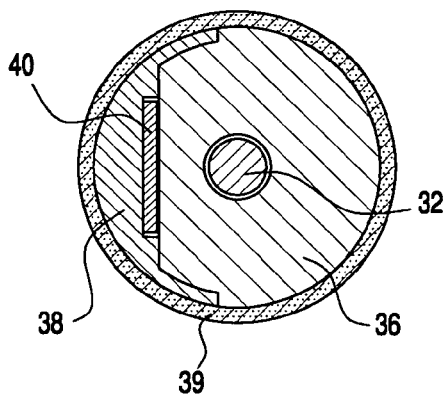

Referring now to FIGS. 2A and 2B, the internal structure of ring 22 is described. In particular, as depicted in FIG. 2A, ring 22 includes flexible tension element 32 having fixed end 33 mounted to first end 26 of the ring and free end 34 that is engaged with motor-driven actuator 35 and extends into a cavity in housing 29. Tension element 32 is slidingly disposed within a substantially cylindrical tube of compressible material 36, e.g., ePTFE, as illustrated in FIG. 2B, so that when tension element is pulled through actuator 35, compressible material 36 is compressed and the diameter of opening 37 is reduced. Compressible material 36 preferably is surrounded on its dorsal face with a flexible, but sturdier elastomeric material, such as silicone element 38. Both compressible material 36 and silicone element 38 preferably are enclosed within a membrane of elastomeric biocompatible material 39, as shown in FIG. 2B, to prevent tissue ingrowth between the ePTFE tube and silicone element 38. Membrane 39 may be affixed to dorsal element 38 using a biocompatible glue to prevent leakage in case of accidental puncture on the dorsal surface.

In accordance with one aspect of the present invention, ring 22 further comprises layer 40 of a relatively rigid material disposed on the dorsal periphery of the ring. Layer 40, which may comprise a plastic or metal alloy, prevents the exterior diameter of ring 22 from changing during adjustment of tension element to reduce internal diameter 37 of the ring. Layer 40, by its structural rigidity, imposes a circular arc shape for the entirety of ring 22. Advantageously, layer 40 allows the tension element to be adjusted following encapsulation of the gastric ring by fibrous tissue after implantation, since adjustment of internal diameter 37 of the gastric ring does not change the external diameter of the ring.

Figures 3A, 3B:
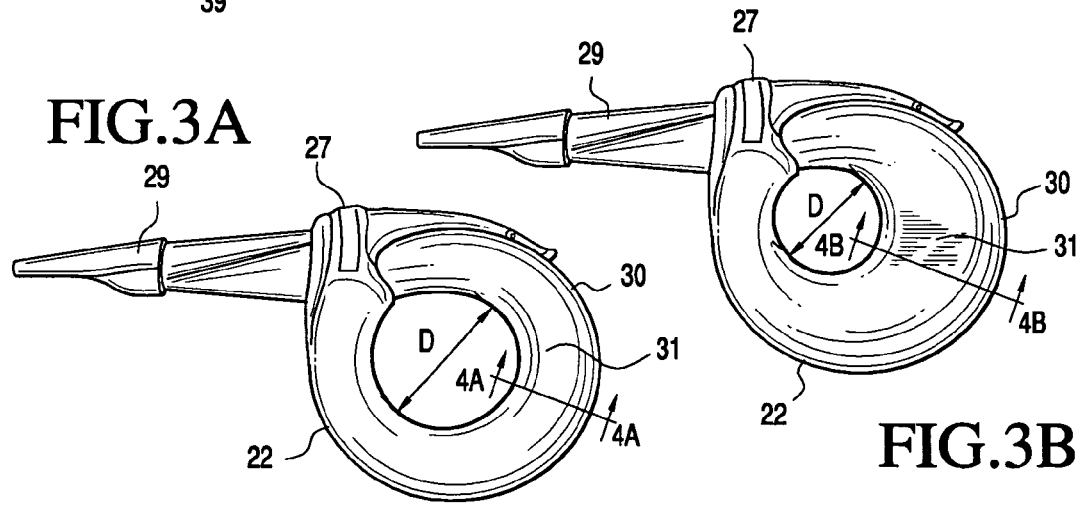
FIGS. 3A and 3B are perspective views illustrating the degree of constriction attainable by the gastric band of the present invention between the fully open and fully closed positions.

The foregoing feature is illustrated in FIGS. 3 and 4. In FIGS. 3A and 3B, ring 22 is shown in its fully open and fully closed positions, respectively. As discussed above, layer 40 forms a rigid skeleton that permits the internal diameter of the ring to change while maintaining the external diameter constant. Radial movement of tension element 32 is transmitted to membrane 39 by compressible material 36. ePFTE is particularly well-suited for use as compressible material 36 because it can undergo a 3:1 reduction in length without experiencing a significant increase in cross-section.

Figure 4A:
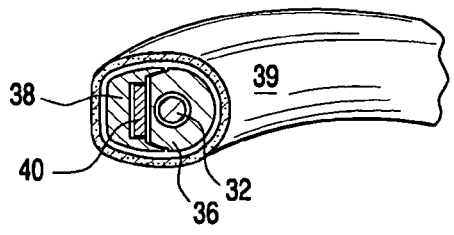
FIGS. 4A and 4B are cross-sectional views of the gastric band of the present invention along the lines 4A-4A and 4B-4B of FIGS. 3A and 3B, respectively.
Figure 4B:
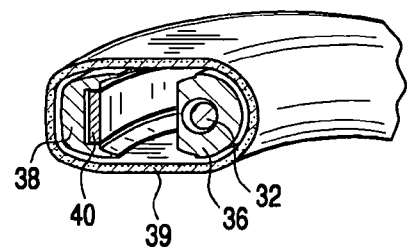

Accordingly, as depicted in FIGS. 4A and 4B, increase or reduction of the length of tension element 32 results in reversible radial displacement at the internal periphery of the ring opposite the dorsal periphery. This in turn translates into a variation of internal diameter D of the ring from a fully open diameter to a fully closed diameter. Preferably, the fully open diameter is about 35 mm, and the fully closed diameter is about 15 mm. More preferably, the fully open diameter is about 29 mm, and the fully closed diameter is about 19 mm.

Figure 5:
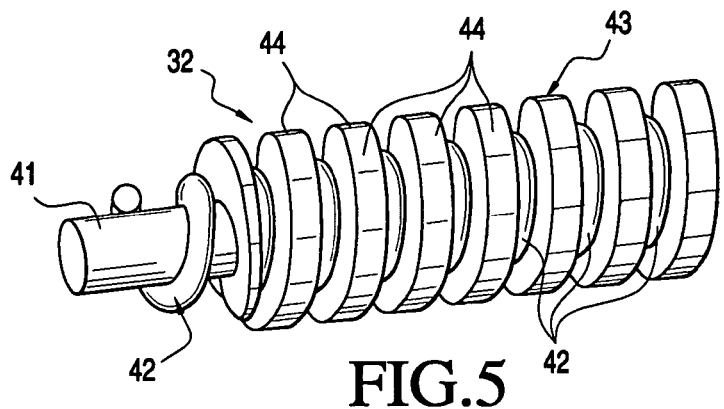
FIG. 5 is a partial perspective view of a screw thread portion of the tension element of the present invention.

Referring now to FIG. 5, tension element 32 is described. Tension element 32 preferably has sufficient flexibility to permit it to be formed into a substantially circular shape of the ring, while also being able to transmit the force necessary to adjust the ring diameter. Tension element 32 therefore comprises flexible core 41, preferably a metal alloy wire of circular cross section, on which is fixed, and wound coaxially, at least one un-joined coil spring which defines the screw thread pitch.

As shown in FIG. 5, tension element 32 preferably comprises two un-joined coil springs that form a screw thread: first spring 42, wound helicoidally along the flexible core 41, and second spring 43 of greater exterior diameter. Second spring 43 preferably comprises coils 44 of rectangular transverse section, so as to delineate a flat external generatrix. First spring 42 is interposed between coils 44 of the second spring 43 to define and maintain a substantially constant square screw thread pitch, even when the tension element is subjected to bending.

As a consequence of the foregoing arrangement, the ability of tension element 32 to maintain a substantially constant thread pitch, when subjected to bending, confers great precision on adjustments of ring 22. This is especially so when it is realized that as the tension element is drawn through actuator 35, an ever-increasing curvature is imposed on the remaining portion of the tension element. However, because the foregoing arrangement of un-joined coils maintains a substantially constant screw thread pitch, the energy needed to drive actuator 35 remains low and the efficiency of energy transmission resulting from the use of a square screw thread pitch remains high. In addition, the use of a square screw thread pitch guarantees a stable adjustment position even when the actuator is unpowered.

Second spring 43 advantageously may be made by laser cutting a cylindrical hollow tube, e.g., made from stainless steel, or alternatively, by winding a wire with a rectangular, trapezoidal or other cross-section. When helically interwound with first spring 42, coils 44 of second spring 43 are naturally activated with an intrinsic elastic compression force from the adjacent coils of first spring 42. As will of course be appreciated, first spring 42 is fixedly joined to flexible core 41 at one end. At the second end, crimped cap 45 (see FIG. 6) is located a short distance from the ends of springs 42 and 43 to allow for small extensions (to accommodate flexion of tension element 32), but also to limit this extension to keep the thread pitch substantially constant.

Figure 6:
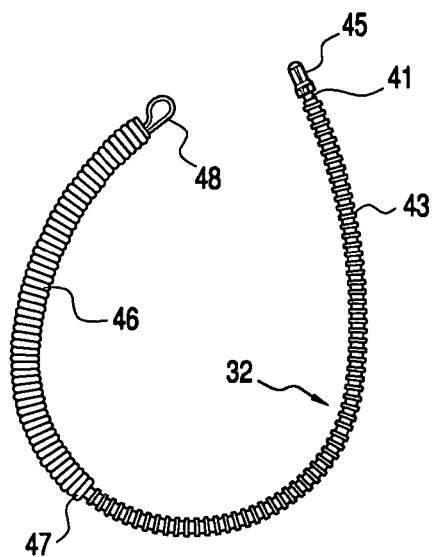
FIG. 6 is a perspective view of an entire tension element suitable for use in the gastric band of the present invention.

Referring now to FIG. 6, the entirety of tension element 32 is described. Free end 34 includes crimped cap 45, second spring 43 having coils with a square transverse section, and first spring 42 (not visible in the figure, but intertwined between the coils of second spring 43). Flexible core 41 extends through first and second springs 42 and 43, and terminates close to cap 45. In accordance with one aspect of the present invention, tension element 32 further comprises third spring 46 that is coupled to flexible core 41, and first and second springs 42 and 43 at junction 47. Third spring 46 includes loop 48 at the end opposite to junction 47, which permits the tension element to be mounted to first end 26 of ring 22.

In accordance with the principles of the present invention, third spring 46 is relatively stiff, but provides a needed degree of compliance to the tension element. Whereas previously-known elastomeric bands provide a small degree of compliance, previously-known non-hydraulic gastric bands, such as disclosed in the above-mentioned Dargent patent have no compliance. Consequently, in the presence of vomiting, which is a frequent complication of gastric bands, previously-known gastric bands prevent convulsive stomach motion, which may result in extreme discomfort to the patient. In the present invention, however, third spring 46 permits the gastric band to temporarily expand due to convulsive activity, and afterwards return to the preselected internal diameter. This feature is expected to significantly reduce patient discomfort and intolerance phenomena.

Figure 7:
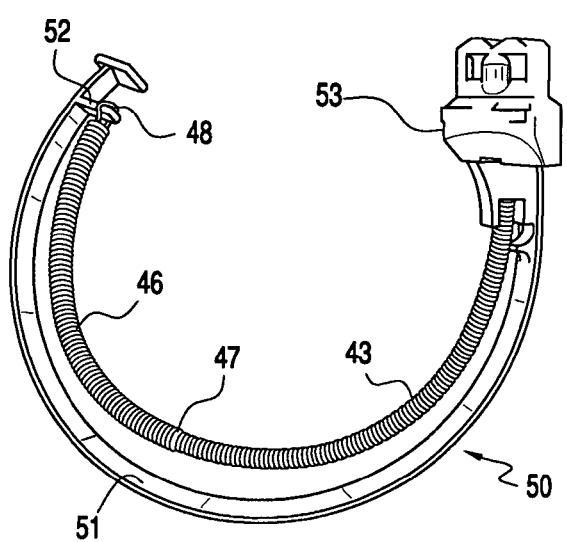
FIG. 7 is a perspective view of the tension element of FIG. 6 coupled to the rigid dorsal peripheral portion and motor housing of the gastric band.
Figure 8:
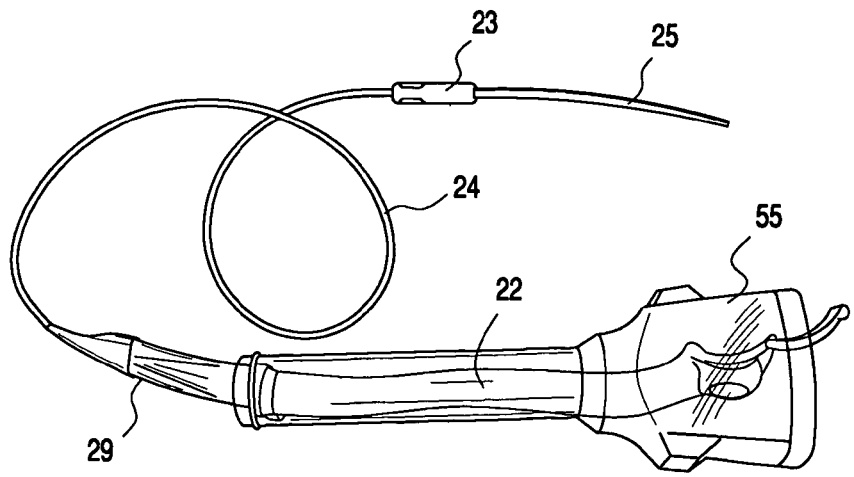
FIG. 8 is a perspective view of the gastric band of FIG. 1 straightened and inserted within a standard 18 mm trocar.

With respect to FIG. 7, tension element 32 is shown disposed within skeleton 50 of the gastric ring 22. Skeleton 50 includes layer 51 that forms the dorsal periphery (corresponding to layer 40 of FIGS. 2 and 4), anchor 52 that accepts loop 48 of tension element 32, and actuator housing 53. Skeleton preferably comprises a high strength moldable plastic. As further depicted in FIG. 7, skeleton 50 extends along a greater arc length than tension element 32. In accordance with another aspect of the present invention, third spring 46 permits gastric band 21 to be straightened for insertion through a standard 18 mm trocar, despite the differential elongation of the skeleton and tension element. This feature'is illustrated in FIG. 8, which depicts ring 22 inserted through 18 mm trocar 55 so that the ring is substantially straight.

Referring now to FIG. 9, housing 29 of the free end of ring 22 is described. Housing 29 comprises an elastomeric material, such as silicone, having recessed portion 56, tension element cavity 57 and cable lumen 58. Recess 56 is configured to accept actuator housing 53 of skeleton 50, so that as tension element 32 is drawn through actuator 35 it extends into tension element cavity 57. Cable lumen 58 extends through housing 29 so that cable 24 may be coupled to actuator 35. Housing 29 preferably may be grasped in area G using atraumatic laparoscopic graspers during manipulation of the device.

In FIG. 10, actuator housing 53 of skeleton 50 is shown with actuator 35 and tension element 32 disposed therethrough. Antenna cable 24 is coupled to motor (not shown) disposed within actuator housing 53. Tension element 32 is in the fully opened (largest diameter) position, so that crimped cap 45 contacts printed circuit board 59 of the reference position switch, described below with respect to FIG. 13.

Actuator

With respect to FIGS. 11 and 12, actuator 35 includes motor 66 coupled to antenna cable 24 that drives nut 60 through gears 61. Nut 60 is supported by upper and lower bearings 62 to minimize energy losses due to friction. Nut 60 is self-centering, self-guiding and provides high torque-to-axial force transfer. Moreover, nut 60 is expected to be more reliable than tangent screw arrangements employed in previously-known mechanical gastric rings, and cannot jump or slip. In addition, nut 60 is self-blocking, meaning that nut 60 will not rotate due to the application of pushing or pulling forces on tension element 32. This condition may be achieved by ensuring that the height (h) of the thread divided by the circumference of the screw ($2\pi R$) is less than the arctangent of the friction coefficient ($\mu$):

$$h/(2\pi R) < \arctan(\mu).$$

Gears 61 preferably are selected to provide good mechanical efficiency, preferably with a reduction factor greater than 1000. In addition, the volume of the actuator depicted in FIGS. 11 and 12 may be quite small, with a total volume less than 1 cm$^3$ and a diameter less than 12.5 mm, so that the device may easily pass through a standard trocar. In a preferred embodiment, gears 61 are selected to provide a force of more than 2 kg on the screw thread of the tension element at an electrical consumption of only 50 mW. The gears and other components of actuator 35 preferably are made of stainless steel or are gold plated to permit operation in the high humidity likely to be encountered in a human body.

Motor 66 employed in actuator 35 preferably comprises a Lavet-type high precision stepper motor with a flat magnetic circuit, such as are used in watches. The motor preferably is a two phase (two coil) motor that permits bi-directional rotation, has good efficiency, and may be supplied with a square wave signal directly by the microcontroller circuitry within antenna/controller pod 35, thus eliminating the need for an interface circuit. Alternatively, the motor employed in actuator 35 may be of a brushless DC type motor. In addition, the motor preferably is compatible with magnetic resonance imaging, i.e., remains functional when exposed to strong magnetic fields used in medical imaging equipment.

Referring now to FIG. 13, the reference position switch of the present invention is described. Because the actuator of the present invention employs nut 60 driven by a stepper motor, there is no need for the system to include a position sensor or encoder to determine the length of tension element 32 drawn through the actuator. Instead, the diameter of ring 22 may be directly computed as a function of the screw thread pitch and the number of rotations of nut 60. To ensure an accurate calculation of the degree of restriction imposed by the gastric ring, however, it is desirable to provide at least one reference point.

This reference datum is accomplished in the gastric ring of the present invention using a reference position switch that is activated when ring 22 is moved to its fully open position. Crimped cap 45 on the free end of tension element 32 serves this function by contacting electrical traces 63 on printed circuit board 59 (and also limits elongation of the screw thread). Circuit board 59 is disposed just above bearing 65, which forms part of actuator 35 (see also FIG. 10). When crimped cap 45 contacts traces 63 it closes a switch that signals the implantable controller that the gastric ring is in the fully open position.

Ring Closure System

With respect to FIGS. 14A and 14B, a preferred embodiment of clip 27 for securing the gastric band in the closed position is described. Clip 27 on first end 26 of the gastric ring includes aperture 70, tab 71 having hinge 72 and slot 73. Aperture 70 is dimensioned to accept second end 28 therethrough, while slot 73 is dimensioned to accept flange 74 disposed on second end 28.

To close ring 22, clip 27 is grasped by the tab 71 and tag 25 of pod 23 (see FIG. 1) is inserted through aperture 70. Clip 27 is then pulled towards second end 28 so that housing 29 passes through aperture 70 while housing 29 is grasped with atraumatic forceps; the conical shape of housing 29 facilitates this action. Force is applied to tab 71 until slot 73 captures flange 74, thereby securing the gastric ring in the closed position. The physician may subsequently choose to disengage slot 73 from flange 74 by manipulating tab 71 using laparoscopic forceps, for example, to reposition the ring. Advantageously, however, forces inadvertently applied to tab 71 in an opposite direction will cause tab 71 to buckle at hinge 72, but will not cause flange 74 to exit slot 73. Accordingly, hinge 72 of tab 71 prevents accidental opening of clip 70 when the tab 71 is subjected to forces that cause the tab to fold backwards away from body 29, such as may arise due to movement of the patient, the organ, of or bolus of fluid passing through the organ.

Antenna/Controller Pod

Figure 15:
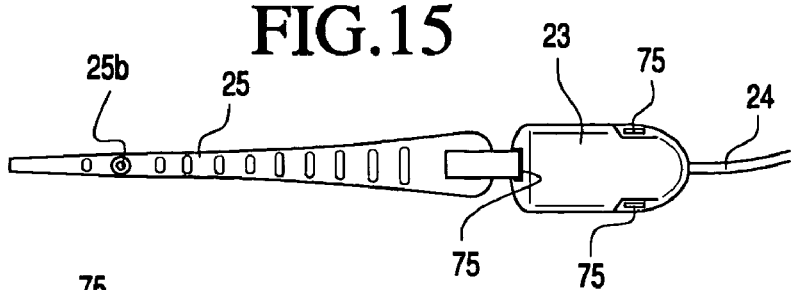
FIG. 15 is a perspective view of the antennae/controller pod of the present invention.
Figure 16:
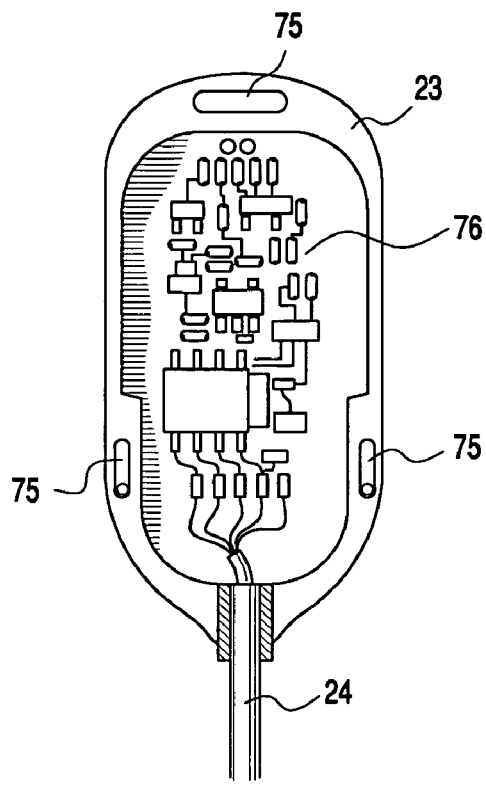
FIG. 16 is a cut-away view of the interior of the implantable antenna/controller pod of FIG. 15.

With respect to FIGS. 15 and 16, antenna/controller pod 23 of the present invention is described. Pod 23 is disposed at the distal end of cable 24 and includes removable tag 25 and holes 75. Tag 25 comprises a grip structure that facilitates manipulation and placement of the pod during implantation; after which the tag is removed using a scissors cut. Tag 25 also includes hole 25b that allows the use of a suture thread to assist in passing the antenna/controller pod 23 behind the stomach. Holes 75 also are dimensioned to be compatible with standard suture needles from size 1-0 to 7-0 to permit pod 23 to be sutured to the patient's sternum, thereby ensuring that pod 23 remains accessible to the external antenna and cannot migrate from a desired implantation site.

As shown in FIG. 16, antenna/controller pod 23 encloses printed circuit board 76 that carries the antenna and microcontroller circuitry of gastric band 22. The antenna receives energy and commands from external control 10 (see FIG. 1), and supplies those signals to the microcontroller, which in turn powers motor 66 of actuator 35. The circuitry of antenna/controller pod 23 uses the energy received from the incoming signal to power the circuit, interprets the commands received from external control 10, and supplies appropriate signals to the motor of actuator 35. The circuit also retrieves information regarding operation of the motor of actuator 35 and relays that information to external control 10 via the antenna. The circuit board preferably is covered with a water-resistant polymeric covering, e.g., Parylene, to permit use in the high (up to 100%) humidity environment encountered in the body.

Antenna/controller pod 23 includes a mechanical closure system that is augmented by silicone glue so that the pod is fluid tight. This silicone glue also is used to protect soldered wires 79 from humidity. The pod preferably is small, e.g., 16 mm×33 mm×4 mm, to ensure compatibility with a standard 18 mm trocar and so as to be compatible with placement on the sternum. The pod preferably has a smooth, atraumatic shape to avoid tissue damage, has good mechanical strength to withstand handling with surgical graspers and to prevent mechanical deformation to the printed circuit board, and has good electromagnetic permeability to allow efficient energy transmission through the pod. Antenna/controller pod 23 preferably has a relatively thin planar configuration to avoid rotation of the pod when placed under the skin, and may include holes that permit the pod to be sutured in position.

Figure 17:
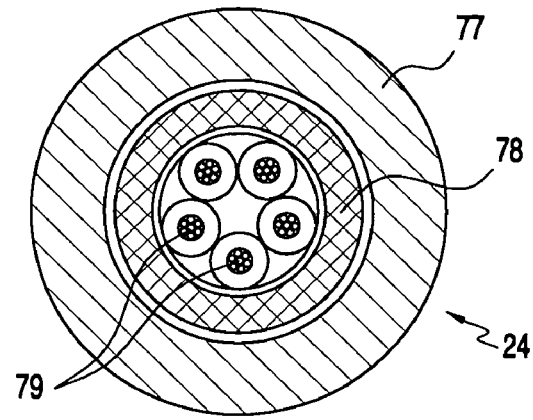
FIG. 17 is a cross-sectional view of the antennae cable of FIG. 15.

With respect to FIG. 17, antenna cable 24 is shown in cross-section. Cable 24 preferably is a coaxial shielded cable encapsulated in a silicone tube 77 to provide biocompatibility. Tube 77 is selected to provide leak-proof encapsulation, with sufficient strength to permit the cable to be manipulated with atraumatic graspers. Braided shield 78 of the cable prevents longitudinal deformation of the cable, and surrounds five helically wound insulated wires 79. Four of wires 79 are used to supply power to the micromotor of actuator 35; the remaining wire and braided shield 78 are used to supply a signal from the reference position switch to the controller.

As discussed above with respect to FIG. 1, the gastric band according to the present invention provides an integrated system for regulating food ingestion in the stomach of a patient, wherein variation of the diameter of the gastric ring may be adjusted without any invasive surgical intervention. To accomplish this, actuator 35 is linked to subcutaneous antenna/controller pod 23 to receive a radio frequency control and power signal. In the preferred embodiment, the motor of the actuator has no internal energy supply, but rather is powered by the receiving circuit of the antenna through a rechargeable energy storage device, such as a capacitor. In particular, the receiving circuit converts radio frequency waves received from external control 10 via the antenna into a motor control and power signal. In an alternative, although less preferred, embodiment the actuator may be driven via an implantable rechargeable battery.

Power and Control Circuitry

Figure 18:
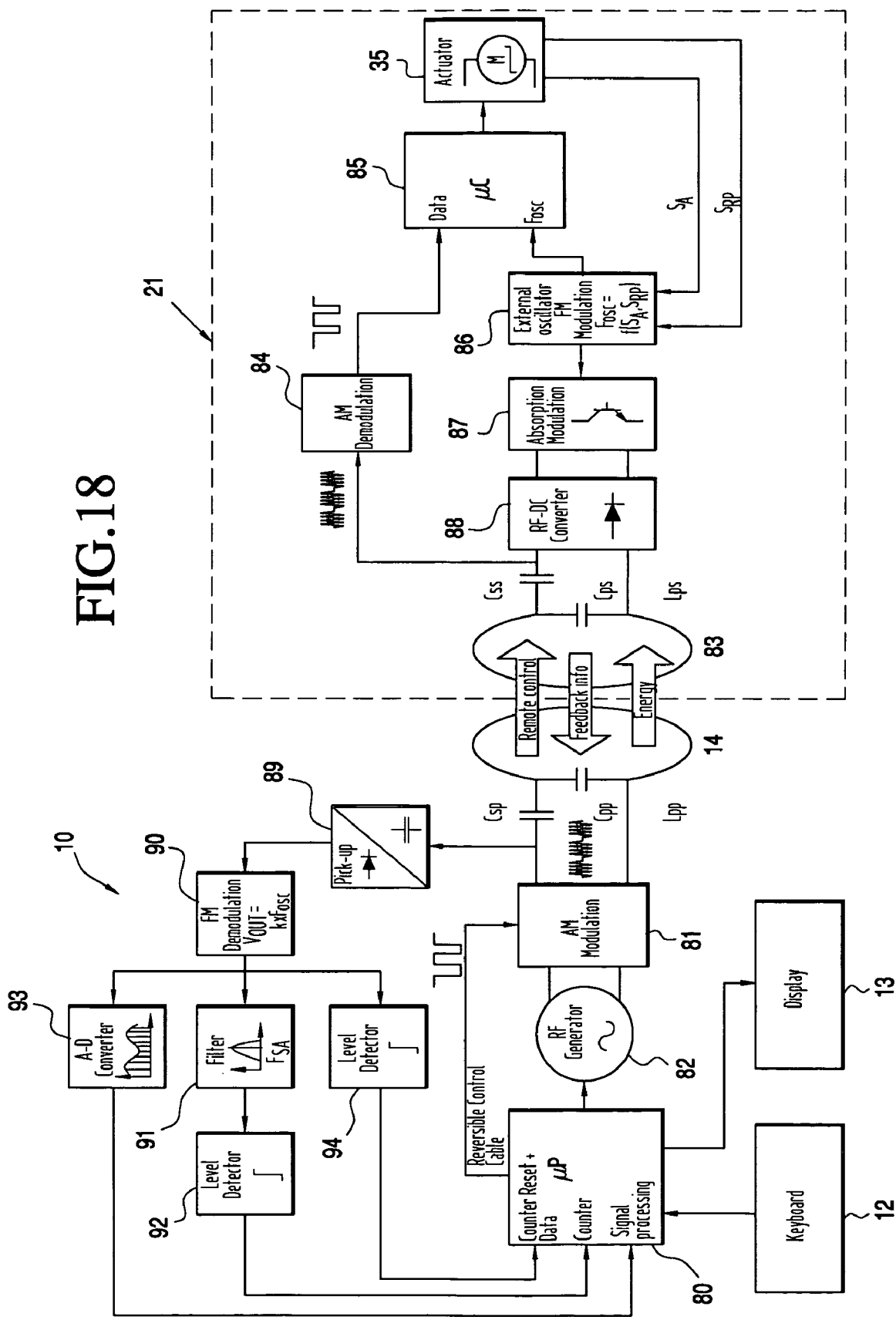
FIG. 18 is a schematic view of the telemetric power and control circuitry of the present invention.

Referring to FIG. 18, a presently preferred embodiment of the circuitry employed in external control 10 and gastric band 22 of the present invention is described, based on the principle of passive telemetry by FM-AM absorption modulation. External control 10 is shown on the left hand side of FIG. 18, and includes microprocessor 80 coupled to control panel 12 and display 13 (see FIG. 1). External control 10 produces a signal comprising one or more data bytes to be transmitted to the implantable antenna/controller pod 23 and actuator 35 (shown on the right hand side of FIG. 18).

External control 10 includes modulator 81 for amplitude modulation of the RF wave from RF generator 82, which signal is emitted by the external antenna 14. The emitted wave is received by the antenna 83 in the antenna/controller pod 23, where AM demodulator 84 extracts the data bytes from the envelope of received RF signal. The data bytes then are decoded and written into an EEPROM of microcontroller 85. A special code is used that allows easy decoding of the data by microcontroller 85, but also provides maximal security against communication failure.

External oscillator 86, which is a voltage controlled oscillator (VCO), provides a clock signal to microcontroller 85. Oscillator 86 may consist of, for example, a relaxation oscillator comprising an external resistor-capacitor network connected to a discharging logic circuitry already implemented in the microcontroller or a crystal oscillator comprising a resonant circuit with a crystal, capacitors and logic circuits. The former solution requires only two additional components, is suitable when the stability of the frequency is not critical, and has low current consumption; the latter solution provides a more stable frequency, but requires a greater number of additional components and consumes more power. Oscillator 86 preferably comprises the external RC network, due to its simplicity.

Microcontroller 86 interprets the received instructions and produces an output that drives the motor of actuator 35. As discussed above, actuator 35 comprises a bi-directional stepper motor that drives nut 60 through a series of reducing gears. Preferably, the two coils of the stepper motor of actuator 35 are directly connected to microcontroller 85, which receives the working instructions from demodulator 84, interprets them and provides the voltage sequences to the motor coils. When the supply of voltage pulses to the stepper motor stops, the gears are designed to remain stationary, even if a reverse torque or force is applied to nut 60 by tension element 32.

As also described above, use of a stepper motor in actuator 35 makes it is possible to obtain positional information on nut 60 and tension element 32 without the use of sensors or encoders, because the displacement of the tension element is proportional to the number of pulses supplied to the stepper motor coils. Two signals are employed to ensure precise control, reference position signal $S_{RP}$, generated by the reference position switch of FIG. 13, and the actuator signal $S_A$.

According to one preferred embodiment, signal $S_A$ is the voltage signal taken at one of the outputs of microcontroller 85 that is connected to the motor coils of actuator 35. Alternatively, signal $S_A$ could be derived from the current applied to a motor coil instead of the voltage, or may be an induced voltage on a secondary coil wrapped around one of the motor coils of actuator 35. In either case, signal $S_A$ is a pulsating signal that contains information on the number of steps turned by the rotor and further indicates whether blockage of the mechanism has occurred. Specifically, if the rotor of the stepper motor fails to turn, the magnetic circuit is disturbed, and by induction, affects signal $S_A$, e.g., by altering the shape of the signal. This disturbance can be detected in the external control, as described below.

Signals $S_A$ and $S_{RP}$ are converted into frequencies using external oscillator 14, so that the voltage level of signal $S_A$ applied to external oscillator 86 causes the oscillator to vary its frequency $F_{osc}$ proportionally to the signal $S_A$. Thus, $F_{osc}$ contains all the information of signal $S_A$. When crimped cap 45 and tension element 32 are in the reference position (gastric ring 22 is fully open), the reference position switch produces reference position signal $S_{RP}$. Signal $S_{RP}$ is used to induce a constant shift of the frequency $F_{osc}$, which shift is easily distinguishable from the variations due to signal $S_A$. If oscillator 86 is a relaxation oscillator, as described above, signals $S_A$ and $S_{RP}$ modify the charging current of the external resistor capacitor network. In this case, the relaxation oscillator preferably comprises an external resistor-capacitor network connected to a transistor and a logic circuit implemented in microcontroller 85. With $S_A$ and $S_{RP}$, the goal is to modify the charging current of the capacitor of the RC network to change the frequency of the relaxation oscillator. If the charging current is low, the voltage of the capacitor increases slowly and when the threshold of the transistor is reached, the capacitor discharges through the transistor. The frequency of the charging-discharging sequence depends on the charging current.

If oscillator 86 is a crystal oscillator, signals $S_A$ and $S_{RP}$ modify the capacitor of the resonant circuit. In this case, the crystal oscillator circuit preferably comprises a crystal in parallel with capacitors, so that the crystal and capacitors form a resonant circuit which oscillates at a fixed frequency. This frequency can be adjusted by changing the capacitors. If one of these capacitors is a Varicap (a kind of diode), it is possible to vary its capacitance value by modifying the reverse voltage applied on it, $S_A$ and $S_{RP}$ can be used to modify this voltage.

In either of the foregoing cases, signals $S_A$ and $S_{RP}$ are used to modify at least one parameter of a resistor-capacitor (RC) network associated with the oscillator 14 or at least one parameter of a crystal oscillator comprising the oscillator 14.

Referring still to FIG. 18, signals $S_A$ and $S_{RP}$, derived from the stepper motor or from the output of the microcontroller 85, may be used directly for frequency modulation by the oscillator 86 without any encoding or intervention by the microcontroller 85. By using oscillator 86 of microcontroller 85 as part of the VCO for the feedback signal, no additional components are required, and operation of micro controller 85 is not adversely affected by the changes in the oscillator frequency $F_{osc}$. The oscillating signal $F_{osc}$ drives voltage driven switch 87 for absorption modulation, such that feedback transmission is performed with passive telemetry by FM-AM absorption modulation.

More specifically, signal $F_{osc}$ drives switch 87 such that during the ON state of the switch 87 there is an increase in energy absorption by RF-DC converter 88. Accordingly, therefore the absorption rate is modulated at the frequency $F_{osc}$ and thus the frequency of the amplitude modulation of the reflected wave detected by external control 10 contains the information for signal $S_A$. As discussed below, pickup 90 in external control 10 separates the reflected wave where it can be decoded by FM demodulation in demodulator 90 to obtain signal $S_A'$. This method therefore allows the transmission of different signals carried at different frequencies, and has the advantage that the ON state of switch 87 can be very short and the absorption very strong without inducing an increase in average consumption. In this way, feedback transmission is less sensitive to variation in the quality of coupling between the antennas 83 and 14.

In external control 10, the feedback signal $F_{osc}$ is detected by the pickup 89 and fed to FM demodulator 90, which produces a voltage output $V_{OUT}$ that is proportional to $F_{osc}$. $V_{OUT}$ is fed to filter 91 and level detector 92 to obtain the information corresponding to the actuator signal $S_A$, which in turn corresponds to the pulses applied to the stepper motor coil. Microprocessor 80 counts these pulses to calculate the corresponding displacement of the tension element 32, which is proportional to the number of pulses.

Signal $V_{OUT}$ also is passed through analog-to-digital converter 93 and the digital output is fed to the microprocessor 80, where signal processing is performed to detect perturbations of the shape of the feedback signal that would indicate a blockage of the rotor of the stepper motor. Microprocessor 80 stops counting any detected motor pulses when it detects that the actuator is blocked, and outputs an indication of this status. Level detector 94 produces an output when it detects that the demodulated signal $V_{OUT}$ indicates the presence of the reference position signal $S_{RP}$ due to activation of the reference position switch. This output induces a reset of the position of the tension element calculated by microprocessor 80 in the external control. In this way, a small imprecision, e.g. an offset, can be corrected.

As described above, external control 10 transmits both energy and commands to the implantable controller circuitry in antenna/controller pod 23. External control 10 also receives feedback information from the implantable controller that can be correlated to the position of the tension element and the diameter of the ring. As will be apparent to one of skill in the art, external control 10 and the implantable controller are configured in a master-slave arrangement, in which the implantable controller is completely passive, awaiting both instructions and power from external control 10.

Operational Modes

Figure 19:
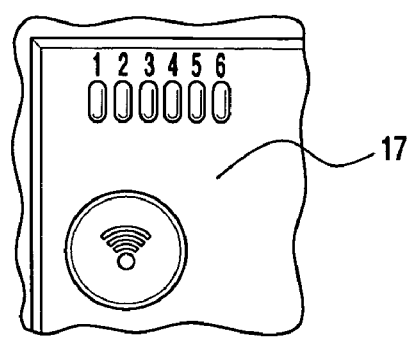
FIG. 19 is a detailed view of the signal strength indicator portion of the remote control of FIG. 1A.

Referring to FIG. 19, some of the safety features of the system of the present invention are described. As discussed above with respect to FIG. 18, both power and control signals are provided to the implantable controller from external control 10. Because power is delivered to the implantable controller via magnetic induction, the amount of energy delivered to the controller depends on the quality of the coupling between external antenna 14 and the antenna circuitry contained within antenna/controller pod 23.

The quality of the coupling may be evaluated by analyzing the level of the feedback signal received by external control 10, and a metric corresponding to this parameter may be displayed on signal strength indicator 17, which includes 6 LEDs (corresponding to six levels of coupling). If the coupling between the antennae is insufficient, the motor of actuator 35 may not work properly, resulting in an inaccurate adjustment of gastric band 21.

Accordingly, in a standard mode of operation, adjustment may be made only if the coupling quality is strong enough, as indicated by having at least LED 5 or LED 6 in FIG. 19 illuminated. If, on the other hand, poor coupling exists (e.g., one of the first four LEDs are illuminated) it is still possible to perform some adjustment of the device, although the adjustment may be inaccurate.

The design of external control 10, in combination with patient microchip card 16 (see FIG. 1), also ensures a high degree of efficacy and safety. First, as contemplated for use with gastric band 21 of the present invention, external control 10 is intended primarily for use by a physician in an office or hospital setting, and not by the patient alone. Of course, in alternative embodiments, such as to treat urinary or fecal incontinence, it would be essential to provide an external control for use by the patient. The simplicity of the design of the external control and ease of use would provide no impediment to use by the patient for such embodiments.

As discussed with respect to FIG. 1, patient microchip card 16 stores, among other data, a serial number identifying a corresponding gastric band and the diameter of the ring upon completion of the previous adjustment. When the external control first transmits energy to the implantable controller of the gastric band, the gastric band identifies itself to the external control. In the standard mode of operation, the serial number stored on the patient microchip card must match that received from the gastric band, otherwise no adjustment is permitted.

As a failsafe, however, the physician still may adjust the gastric band even if the patient has lost or misplaced his microchip card. In this case, the external control may be set in a "no card mode." In this mode, the information displayed on display 13 of the exterior control corresponds only to the relative variation of the gastric band during that adjustment session, and is no longer indicative of absolute diameter. When the physician activates this mode, an emergency bit is set in the memory of the implantable controller to indicate the "no card mode." In subsequent adjustment sessions, the implantable controller will signal that the gastric band was adjusted in the "no card mode" and all further adjustments will be reported on a relative basis. If the patient again locates the microchip card, the emergency bit may be cleared by fully opening the gastric band and thus reaching the reference contact, which re-initializes the position. Subsequent adjustments will again be managed in the standard mode of operation.

During adjustment of the gastric ring physician places external antenna 14 in a face-to-face position on the skin of the patient relative to antenna/controller pod 23 of the gastric ring, and to receive feedback information from which the constricted diameter of the gastric ring may be computed. In accordance with the principles of the present invention, it is possible to vary the diameter of the gastric ring without having to undertake invasive surgical intervention, and this variation may be carried out at will, because multiple control cycles may be carried out at regular or irregular intervals, solely under the control of the treating physician.

The gastric band system of the present invention is expected to be particularly reliable, relative to previously-known hydraulic bands that can be adjusted by the patient, because only the physician typically will have access to the external control box needed to adjust the ring. For a ring embodiment intended for treatment of morbid obesity, the patient therefore does not have free access to any means to adjust the diameter of the ring.

Moreover, because the gastric band of the present invention provides a precise readout of the current diameter of the ring in the standard mode of operation, it may not be necessary for the patient to ingest a radiographic material (e.g., barium dye) to permit radiographic visualization of the ring to confirm the adjusted size. The process of adjusting the band accordingly may be carried out in a doctor's office, without the expense associated with radiographic confirmation of such adjustments. In addition, the self-blocking configuration of the tension element and nut, in combination with the mechanical nature of the gastric band, overcome problems associated with previously-known hydraulically-actuated gastric band systems.

Methods of Implantation and Removal

Figure 20:
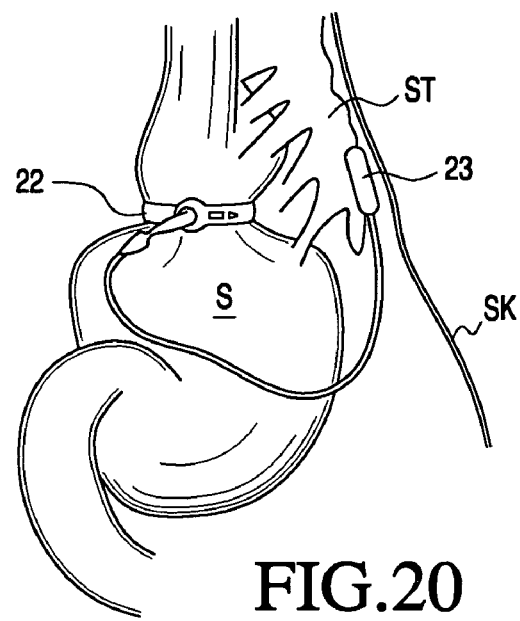
FIG. 20 is a schematic diagram illustrating placement of the implantable portion apparatus of the present invention within a patient.

Referring now to FIG. 20, gastric band 21 of the present invention is shown implanted in a patient. Ring 22 is disposed encircling the upper portion of the patient's stomach S while antenna/controller pod 23 is disposed adjacent to the patient's sternum ST. Pod 23 is located in this position beneath the patient's skin SK so that it is easily accessible in the patient's chest area to facilitate coupling of the pod 23 to external antenna 14 of external control 10 (see FIG. 1).

Figure 21A:
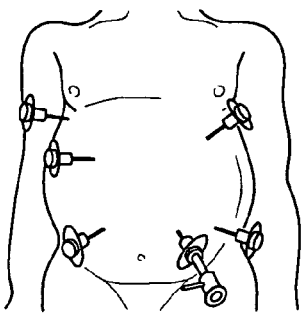
FIGS. 21A-21H are views illustrating a method of laparoscopically implanting the gastric band of the present invention.

Referring to FIGS. 21A to 21H, a method of implanting the gastric band of the present invention is described. The method is similar to laparoscopic procedures used to implant previously-known hydraulically-actuated gastric bands. Access to the abdomen is obtained by using 4 to 6 small holes, generally 10 to 18 mm in diameter, with a trocar inserted in each hole, as depicted in FIG. 21A. A camera and laparoscopic surgical tools are introduced and manipulated through the trocars. In addition, to permit free motion of the surgical tools and camera, the abdomen is inflated with $CO_2$ to an overpressure of approximately 0.15 bars.

Figure 21B:
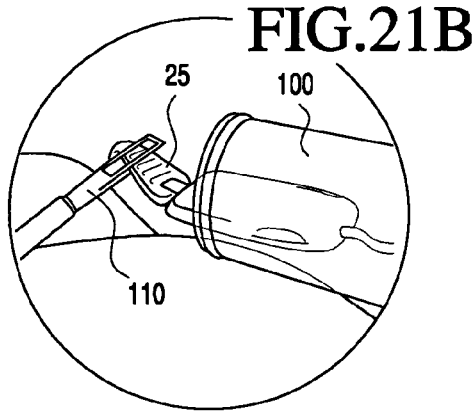
Figure 21C:
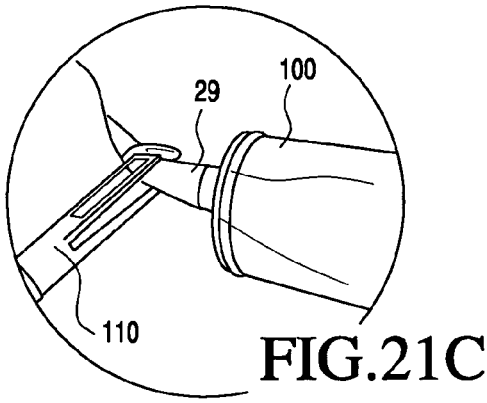
Figure 21D:
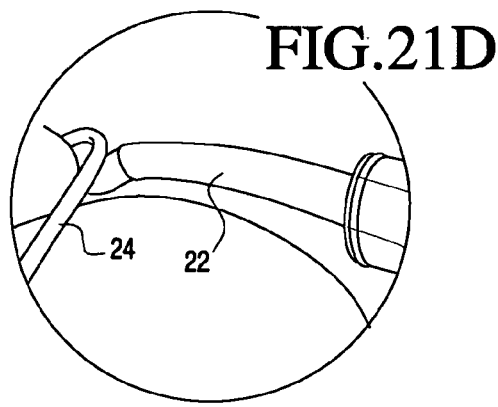
Figure 21E:
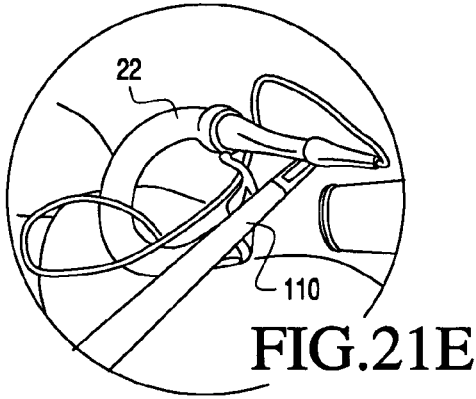

In FIGS. 21B-21E, the gastric band of the present invention is straightened (as depicted in FIG. 8) and inserted, antenna first, into the abdomen through an 18 mm trocar. Alternatively, a laparoscopic cannula may be used to make an incision and then withdrawn, and the device inserted through the opening so created (other instruments also may be used to form this laparotomy). In FIG. 21B, tag 25 of antenna/controller pod 23 is shown entering the abdomen through trocar 100 using atraumatic graspers 110. In FIG. 21C, housing 29 of the gastric ring is shown being drawn into the abdomen through trocar 100, again using atraumatic graspers 110. FIG. 21D shows ring 22 entering the abdomen in an extended position. In FIG. 21E, the ring is permitted to resume its preferred ring shape.

Figure 21F:
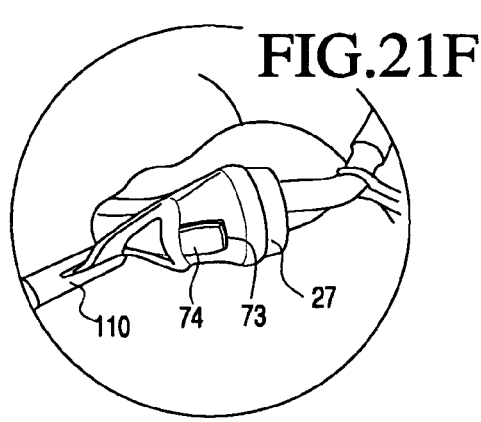

Ring 22 then is manipulated using atraumatic graspers 100 (as described above with respect to FIGS. 14A and 14B) to secure the gastric ring around the upper portion of the patient's stomach until slot 73 of clip 27 is engaged with flange 74, as shown in FIG. 21F. A fold of stomach tissue then may be sutured around the gastric ring to prevent migration of the gastric band, as is typical for hydraulically-actuated gastric bands.

Figure 21G:
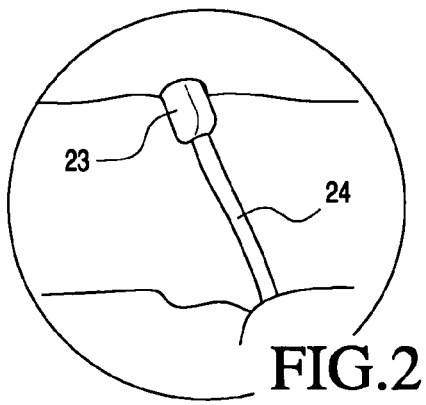
Figure 21H:
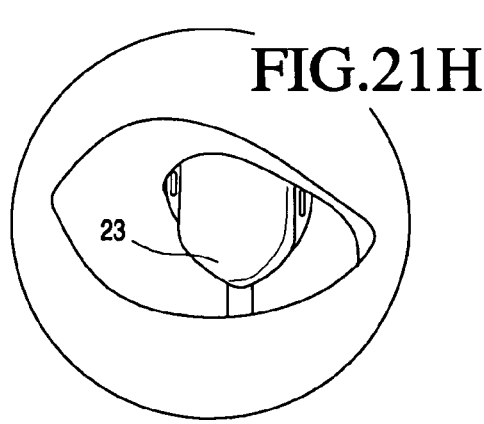

Finally, as shown in FIG. 21G, a channel may be formed through the abdominal wall and antenna/controller pod 23 passed through the channel. Tag 25 then is cut off of antenna/controller pod 23, and the pod is sutured into position above the patient's sternum, as depicted in FIG. 21H. The trocars then are removed, and the gastric band may be activated to adjust the diameter of the ring as desired by the physician.

The process of removing the gastric ring of the present invention involves substantially reversing the sequence of steps described above, and may be accomplished non-destructively. In particular, a plurality of cannulae into the abdominal cavity and the abdominal cavity then insufflated to create a pneumoperitoneum. Using laparoscopic graspers, the clip of the gastric ring may be unclipped and the elongated member removed from a position encircling the patient's stomach. The gastric ring may then be straightened and withdrawn from the abdominal cavity either through one of the plurality of cannulae or via a laparotomy.

Other Features

The gastric band of the present invention contains several airspaces as a result of its design, and applicants have observed that some precautions are required when implanting the gastric band. In particular, airspaces within ring 22 typically contain air, which is approximately 80% $N_2$, and much of the ring is encapsulated in a thin leak-proof silicone membrane (see FIGS. 2 and 4). Because this membrane permits $CO_2$ to diffuse into the ring about 20 times faster than the entrapped $N_2$ can diffuse out, significant swelling of the membrane may result when the gastric ring is inserted into an abdomen expanded with $CO_2$. Once the $N_2$ and $CO_2$ pressures equilibrate, the swelling resolves, typically in about three hours.

While the membrane is distended, however, there is a risk that the membrane may be pierced, for example, by the sharp needles employed to suture the fold of stomach tissue over the ring, or to suture the antenna/controller pod in position. Applicants accordingly have devised four solutions to address this issue: (1) $CO_2$ preconditioning; (2) $CO_2$ packaging; (3) a valve system; and (4) use of a less extensible membrane.

$CO_2$ preconditioning refers to placing the gastric band in a $CO_2$-filled container for a specified duration, e.g., 3 hours, prior to implantation to permit the $N_2$ and $CO_2$ pressures to equilibrate prior to implantation. The gastric ring may be sealed within sterile packaging prior to such preconditioning. $CO_2$ packaging refers to packaging the gastric band in $CO_2$-filled container during the manufacturing process, so that no substantial swelling arises during the implantation procedure. Use of a valve system would entail implementing a pressure-relied valve on the membrane of the ring to avoid the build up of overpressure within the device, while preventing bodily fluids from ingressing into the device. Finally, the choice of a different membrane material or thickness may be used to control the swelling phenomena. During initial clinical testing of the device the preconditioning option is expected to be used, although $CO_2$ packaging is contemplated as the most expedient solution for commercial manufacture. Other gases than carbon dioxide may be used to expand the abdomen, and such alternative preselected gases likewise may be used to precondition the gastric ring of the present invention.

As stated in the Overview portion of the present application, the telemetrically-powered and controlled ring system of the present invention has numerous applications apart from gastric banding for the treatment of morbid obesity. For example, the ring system of the present invention may advantageously be used for the treatment of fecal incontinence, ileostomy, coleostomy, gastro-esophageal reflux disease, urinary incontinence and isolated-organ perfusion.

For treatment of fecal incontinence, the ring may be used with little or no modifications. In addition, because the ring adjustment procedure will be performed by the patient on at least a daily basis, a portable user-friendly external control may be used. In addition, because the ring will regularly be transitioned between the closed and fully opened position, the patient microchip card is unneeded. Instead, the fully closed position may be stored in the memory of the implantable controller, and read by the external remote at each use (subject to periodic change by the physician).

A similarly modified device could be used by patients who have undergone ileostomy or coleostomy, or disposed surrounding the esophageal junction, to treat gastro-esophageal reflux disease.

For treatment of urinary incontinence, the ring may be further modified to minimize the volume of the ring surrounding the urethra by moving the actuator motor to a location elsewhere in the lower abdomen or pelvis, and coupling the actuator to the motor via a transmission cable.

The present invention also may be beneficially employed to perform isolated-organ perfusion. The treatment of certain cancers requires exposure to levels of chemotherapy agents that are too high for systemic circulation. It has been suggested that one solution to this problem is perform an open surgery procedure in which blood flow to the cancerous organ is stopped and quiescent blood replaced by circulation from an external source containing a desired dose of drug. Individual or multiple rings of the present invention may be used as valves to isolate the cancerous organ and permit perfusion of the organ with high doses of drugs. Such procedures could thus be performed on a repetitive basis without surgery, thereby reducing the trauma and the risk to the patient while improving patient outcomes.

Although particular embodiments of the present invention have been described above in detail, it will be understood that this description is merely for purposes of illustration. Further variations will be apparent to one skilled in the art in light of this disclosure and are intended to fall within the scope of the appended claims.

What is claimed is:

1. A method of laparoscopically implanting a gastric band comprising a telemetrically-driven mechanical actuator within a patient's abdominal cavity to control passage of food through the patient's stomach, the method comprising:

providing a gastric band comprising an elongated member having a flexible element sealingly encapsulated in the elongated member, the flexible element defining a helical screw thread having a core wire and a first helical spring disposed on the core wire, the first helical spring having a rectangular or a trapezoidal transverse profile, the helical screw thread having a second helical spring interwound with the first helical spring to define a pitch of the first helical spring, and the gastric band having a telemetrically-driven mechanical actuator that engages the helical screw thread to selectively constrict the elongated member against the patient's stomach;

inserting a plurality of cannulae into the abdominal cavity;

insufflating of the abdominal cavity to create a pneumoperitoneum;

dissecting tissue surrounding the stomach to create a path for the elongated member using a first tool inserted into one of the cannulae;

introducing the gastric band into the abdominal cavity;

grasping the gastric band with a second tool placed through a cannula; and manipulating the elongated member to encircle the patient's stomach and form a stoma opening within the stomach.

2. The method of claim 1 wherein grasping the gastric band with a second tool placed through a cannula comprises grasping the gastric band using laparoscopic instruments.

3. The method of claim 1 wherein manipulating the elongated member to encircle the patient's stomach comprises manipulating the elongated member using laparoscopic instruments.

4. The method of claim 1 wherein introducing the gastric band into the abdominal cavity comprises introducing the gastric band via a laparoscopic cannula.

5. The method of claim 1 wherein introducing the gastric band into the abdominal cavity comprises introducing the gastric band via a laparotomy.

6. The method of claim 1 further comprising preconditioning the gastric band in a preselected gas.

7. The method of claim 6, wherein the preconditioning comprises placing the gastric band within a container having a preselected gas atmosphere for a sufficient duration.

8. The method of claim 7 wherein the gastric band is sealed within sterile packaging prior to preconditioning.

9. The method of claim 6 wherein preconditioning the gastric band comprises packaging the gastric band in a sealed container having a preselected gas atmosphere.

10. The method of claim 1 wherein the gastric band further comprises an antenna coupled to the telemetrically-driven mechanical actuator, the method further comprising manipulating the antenna using laparoscopic instruments to locate the antenna subcutaneously atop the patient's sternum.

11. The method of claim 10 further comprising suturing the antenna in position.

12. The method of claim 1 wherein the elongated member comprises first and second ends and a clip disposed on the first end, wherein manipulating the elongated member to encircle the patient's stomach comprises manipulating the elongated member so that the clip engages the second end.

13. The method of claim 12 wherein the clip comprises an aperture configured to receive the second end, the method further comprising manipulating the second end of the elongated member to insert it through the clip.

14. The method of claim 12 wherein the elongated member further comprises a compressible ventral surface and a substantially rigid dorsal periphery, the method further comprising straightening the elongated member to permit passage into the abdominal cavity.

15. The method of claim 12 further comprising:
providing a remote control; and
telemetrically operating the telemetrically-driven actuator to confirm proper operation of the gastric band.

16. The method of claim 15 wherein telemetrically operating the telemetrically-driven actuator comprises transmitting power to the telemetrically-controlled actuator via electromagnetic induction.

17. The method of claim 15 further comprising assessing a coupling strength between the remote control and the telemetrically-driven actuator.

18. The method of claim 15 wherein telemetrically operating the telemetrically-driven actuator comprises operating the telemetrically-driven actuator to adjust a diameter of the stoma opening in fine increments.

19. The method of claim 15 wherein telemetrically operating the telemetrically-driven actuator further comprises telemetrically operating the telemetrically-driven actuator so that the remote control receives feedback indicating positional data for the flexible element.

20. The method of claim 1 wherein portions of the gastric band are different colors, wherein manipulating the elongated member to encircle the patient's stomach further comprises manipulating selected portions of the gastric band in accordance with colors of the selected portions of the gastric band.

21. A method of laparoscopically implanting a gastric ring comprising a telemetrically-driven actuator within a patient's abdominal cavity to control passage of food through the patient's stomach, the method comprising:

providing a gastric ring comprising an elongated member having a first end and a second end, a housing disposed on the second end of the elongated member, an electric motor disposed within the housing, a nut actuator disposed within the housing and coupled to the electric motor, a flexible element sealingly encapsulated in the elongated member, the flexible element defining a helical screw thread that engages and extends through the nut actuator, operation of the nut actuator causing the helical screw thread to selectively constrict the elongated member against the patient's stomach;

placing at least one laparoscopic cannula within the abdominal cavity;

insufflating the abdominal cavity to create a pneumoperitoneum;

placing at least two additional laparoscopic cannulae within the abdominal cavity;

dissecting tissue surrounding the stomach to create a path for the gastric ring;

introducing the gastric ring into the abdominal cavity;

grasping the gastric ring with a tool placed through one of the cannulae;

pulling the gastric ring into an encircling position around the stomach; and securing the gastric ring in the encircling position around the stomach.

22. The method of claim 21 wherein grasping the gastric ring with a tool placed through one of the cannulae comprises grasping the gastric ring using a laparoscopic instrument.

23. The method of claim 21 wherein pulling the elongated member to encircle the patient's stomach comprises manipulating the elongated member using laparoscopic instruments.

24. The method of claim 21 further comprising pre-conditioning the gastric ring in a preselected gas atmosphere.

25. The method of claim 24, wherein the preconditioning comprises placing the gastric ring within a container having the preselected gas atmosphere for a sufficient duration.

26. The method of claim 25 wherein the gastric ring is sealed within sterile packaging prior to preconditioning.

27. The method of claim 25 wherein preconditioning the gastric ring comprises packaging the gastric ring in a sealed container having a preselected gas atmosphere.

28. The method of claim 21 wherein the gastric ring further comprises an antenna coupled to the nut actuator, the method further comprising:
manipulating the antenna using laparoscopic instruments to locate the antenna subcutaneously atop the patient's sternum.

29. The method of claim 28 further comprising suturing the antenna in position.

30. The method of claim 21 wherein the elongated member comprises a clip disposed on the first end, wherein securing the gastric ring in the encircling position around the stomach comprises manipulating the elongated member so that the clip engages the second end.

31. The method of claim 30 wherein the clip comprises an aperture configured to receive the second end, the method further comprising manipulating the second end of the elongated member to insert it through the clip.

32. The method of claim 30 further comprising straightening the elongated member to permit passage through the laparoscopic cannula into the abdominal cavity.

33. The method of claim 21 further comprising:
providing a remote control; and
telemetrically operating the nut actuator to confirm proper operation of the gastric ring.

34. The method of claim 33 wherein telemetrically operating the telemetrically-driven nut actuator comprises transmitting power to the actuator via electromagnetic induction.

35. The method of claim 33 further comprising assessing a coupling strength between the remote control and the nut actuator.

36. The method of claim 33 wherein telemetrically operating the nut actuator comprises operating the nut actuator to adjust a length of the flexible element in predetermined increments.

37. The method of claim 33 wherein telemetrically operating the nut actuator further comprises receiving feedback indicating positional data for the flexible element.

38. The method of claim 21 wherein portions of the gastric ring are different colors, wherein pulling the gastric ring into an encircling position around the stomach further comprises manipulating selected portions of the gastric ring in accordance with colors of the selected portions of the gastric ring.

39. The method of claim 21 wherein introducing the gastric ring into the abdominal cavity comprises introducing the gastric ring via a laparoscopic cannula.

40. The method of claim 21 wherein introducing the gastric ring into the abdominal cavity comprises introducing the gastric ring via a laparotomy.

41. A method of laparoscopically implanting a gastric band comprising a telemetrically-driven mechanical actuator within a patient's abdominal cavity to control passage of food through the patient's stomach, the method comprising:
providing a gastric band comprising an elongated member having a first end and a second end, the elongated member further having a flexible element sealingly encapsulated in the elongated member, the flexible element defining a helical screw thread, the gastric band having a telemetrically-driven mechanical nut actuator, the helical screw thread engaging and extending through the telemetrically-driven mechanical nut actuator, operation of the telemetrically-driven mechanical nut actuator causing the helical screw thread to selectively constrict the elongated member against the patient's stomach;
inserting a plurality of cannulae into the abdominal cavity;
insufflating of the abdominal cavity to create a pneumoperitoneum;
dissecting tissue surrounding the stomach to create a path for the elongated member using a first tool inserted into one of the cannulae;
introducing the gastric band into the abdominal cavity;
grasping the gastric band with a second tool placed through a cannula; and
manipulating the elongated member to encircle the patient's stomach and form a stoma opening within the stomach.

42. A method of laparoscopically implanting a gastric ring comprising a telemetrically-driven actuator within a patient's abdominal cavity to control passage of food through the patient's stomach, the method comprising:
providing a gastric ring comprising an elongated member having a first end and a second end, a housing disposed on the second end of the elongated member, an electric motor disposed within the housing, an actuator disposed within the housing and coupled to the electric motor, a flexible element sealingly encapsulated in the elongated member, the flexible element defining a helical screw thread that engages the actuator, the helical screw thread having a core wire and a first helical spring disposed on the core wire, the first helical spring having a rectangular or a trapezoidal transverse profile, the helical screw thread having a second helical spring interwound with the first helical spring to define a pitch of the first helical spring;
placing at least one laparoscopic cannula within the abdominal cavity;
insufflating the abdominal cavity to create a pneumoperitoneum;
placing at least two additional laparoscopic cannulae within the abdominal cavity;
dissecting tissue surrounding the stomach to create a path for the gastric ring;
introducing the gastric ring into the abdominal cavity;
grasping the gastric ring with a tool placed through one of the cannulae;
pulling the gastric ring into an encircling position around the stomach; and
securing the gastric ring in the encircling position around the stomach.

* * * * *

UNITED STATES PATENT AND TRADEMARK OFFICE
CERTIFICATE OF CORRECTION

| | | |
|---|---|---|
| PATENT NO. | : 7,901,419 B2 | Page 1 of 1 |
| APPLICATION NO. | : 10/962852 | |
| DATED | : March 8, 2011 | |
| INVENTOR(S) | : Michel Bachmann et al. | |

It is certified that error appears in the above-identified patent and that said Letters Patent is hereby corrected as shown below:

In column 2, line 27, delete "nevertheless-suffers" and insert -- nevertheless suffers --, therefor.

In column 3, line 52, delete "gastic" and insert -- gastric --, therefor.

In column 4, line 59, delete "may-be" and insert -- may be --, therefor.

In column 18, line 20, delete "coleostomy," and insert -- colostomy, --, therefor.

In column 18, line 33, delete "coleostomy," and insert -- colostomy, --, therefor.

In column 18, line 47, delete "quiescient" and insert -- quiescent --, therefor.

Signed and Sealed this
Thirty-first Day of May, 2011

David J. Kappos
*Director of the United States Patent and Trademark Office*